United States Patent [19]

Pickrell, Jr. et al.

[11] Patent Number: 5,005,730
[45] Date of Patent: Apr. 9, 1991

[54] ORTHODONTIC DISPENSER

[75] Inventors: Floyd W. Pickrell, Jr., Anaheim; James F. Reher, Pomona; Terry L. Sterrett, Long Beach, all of Calif.

[73] Assignee: Ormco Corporation, Glendora, Calif.

[21] Appl. No.: 271,298

[22] Filed: Nov. 15, 1988

[51] Int. Cl.⁵ .............................................. A61C 7/00
[52] U.S. Cl. ...................................... 221/71; 433/3; 433/18
[58] Field of Search ................... 221/25, 26, 70, 71, 221/72, 73, 74, 77, 78; 206/339, 390, 805, 820; 433/3, 4, 18

[56] References Cited

U.S. PATENT DOCUMENTS

| | | | |
|---|---|---|---|
| 2,186,302 | 1/1940 | Martin | 221/72 X |
| 2,289,642 | 7/1942 | Flood . | |
| 3,006,502 | 10/1961 | Tobey | 221/73 |
| 3,193,094 | 7/1965 | Schulstad . | |
| 3,267,623 | 8/1966 | Block | 206/390 X |
| 4,038,753 | 8/1977 | Klein . | |
| 4,106,374 | 8/1978 | Dragan . | |
| 4,217,686 | 8/1980 | Dragan . | |
| 4,330,271 | 5/1982 | Anderson . | |
| 4,436,510 | 3/1984 | Klein | 221/310 X |
| 4,576,311 | 3/1986 | Wiggs et al. . | |
| 4,576,311 | 3/9186 | Horton et al. . | |
| 4,626,313 | 12/1986 | Karp . | |

Primary Examiner—F. J. Bartuska
Attorney, Agent, or Firm—Marjama & Pincelli

[57] ABSTRACT

An orthodontic dispensing device for dispensing orthodontic appliances formed in an elastomeric strip of material. The device comprises a housing having a discharge opening and a guide bar adjacent thereto. A drive reel is provided for moving the strip around the guide bar is provided so as to present the orthodontic appliance for dispensing thereof.

11 Claims, 3 Drawing Sheets

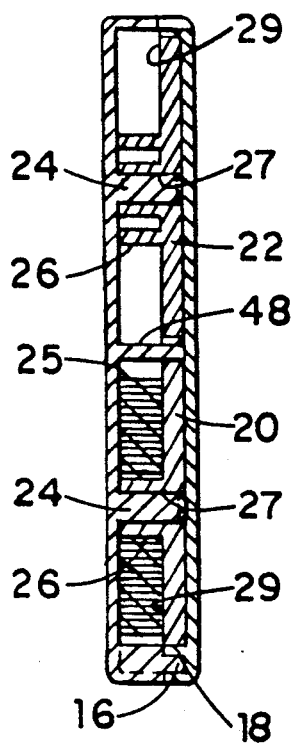
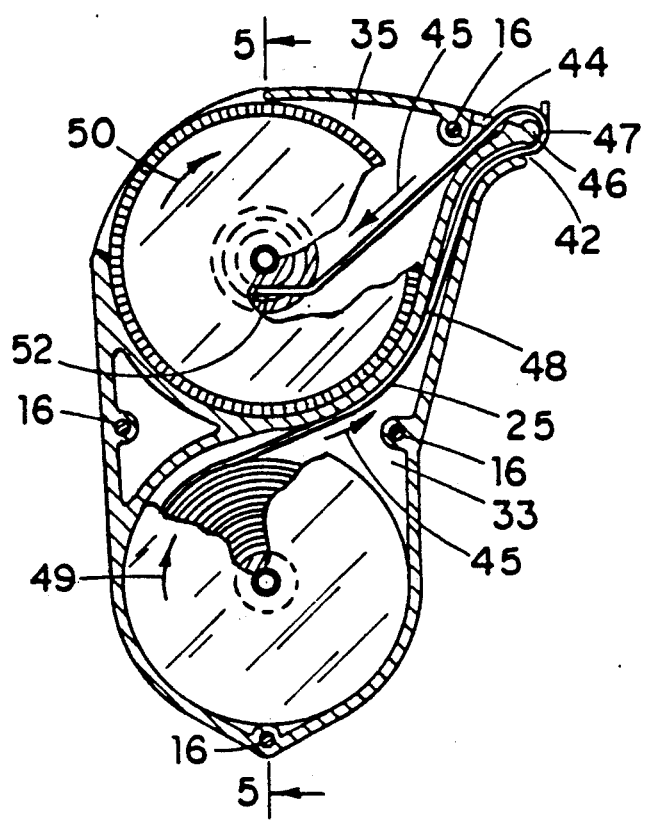
FIG. 5                FIG. 4
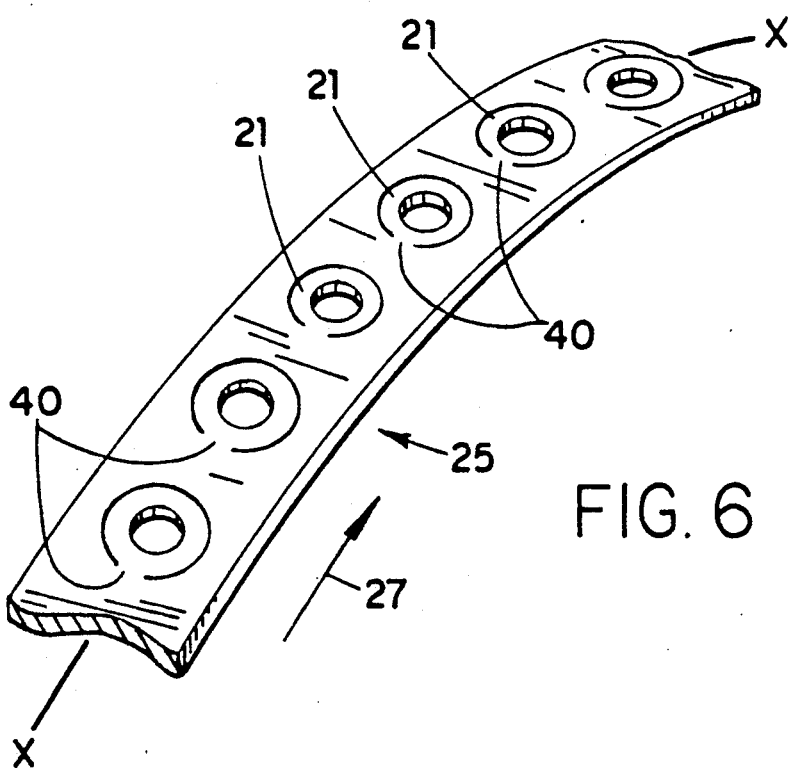
FIG. 6

ORTHODONTIC DISPENSER

BACKGROUND OF THE INVENTION

This invention relates to devices for dispensing orthodontic appliances which are formed in an elastomeric strip of material.

The present invention is particularly suited for dispensing elastomeric devices such as orthodontic O-rings used for securing orthodontic brackets to an orthodontic arch wire. Typically, these O-rings are provided either individually in packages, or are molded on an elongated core. Examples of prior art devices wherein the appliances are molded on a support structure are illustrated by U.S. Pat. Nos. 3,193,094; 4,038,753; and 4,217,686. Typically, these dispensing devices are sold in packages containing a plurality of dispensing devices. When it is desired to use an orthodontic dispensing device, it is simply pulled out of the package and used. This not only exposes the desired dispensing device to the environment, but also exposes the other dispensing devices not used.

In today's orthodontic procedures, a strong concern and effort has been made to maintain the aseptic qualities of the orthodontic procedures. A problem with dispensing devices of the prior art is that contamination can result simply from the manner in which the orthodontic appliances are dispensed. Due to the flexible nature and manner of dispensing the appliances of the prior art, at least some manipulation of the dispensing device with the hands of the user is generally required to dispense the appliances. The handling of the dispensing device typically occurs in the vicinity of the appliances to be dispensed and this subjects these appliances to potential contamination. Additionally, if not all of the orthodontic appliances are not used on a single treatment, the remaining appliances will be simply discarded to avoid any possible contamination resulting from storage.

Applicants have invented an improved dispensing device whereby the aseptic qualities of the orthodontic O-rings are maintained while avoiding contact with undispensed appliances. Additionally, unnecessary waste of O-rings is minimized.

SUMMARY OF THE INVENTION

A dispensing device for dispensing orthodontic appliances formed in an elastomeric strip of material. The device comprises a housing having a discharge opening and a guide bar adjacent thereto. Means for moving the strip of elastomeric material about the guide bar is provided so as to present the orthodontic appliances at the opening for dispensing thereof.

DESCRIPTION OF THE DRAWINGS

FIG. 4 is an cross sectional view of the assembled device of FIG. 2 taken along line 4—4, with the reels partially broken away to illustrate the elastomeric strip;

FIG. 5 is a cross sectional view of the device of FIG. 4 as taken along line 5—5;

FIG. 6 is an enlarged view of a portion of the elastomeric strip placed in the device of FIG. 1;

DETAILED DESCRIPTION OF THE INVENTION

Figure 1:
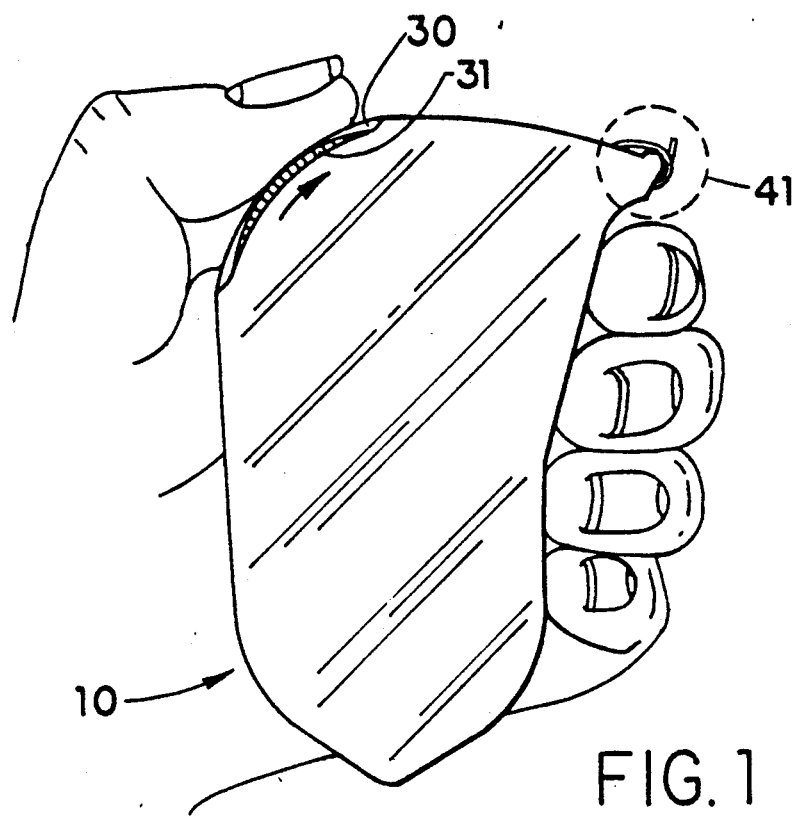
FIG. 1 illustrates top plan view of a dispensing device made in accordance with the present invention.
Figure 2:
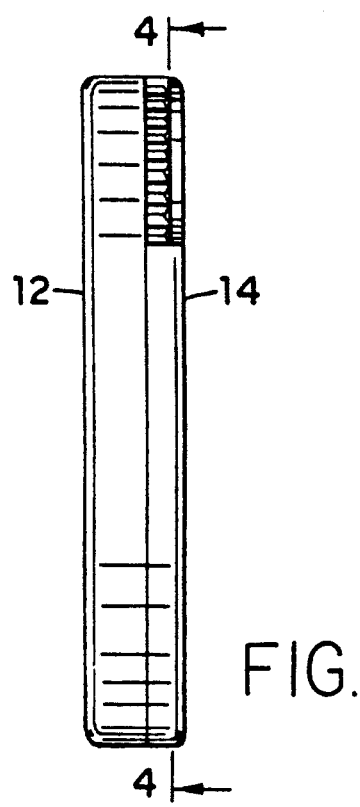
FIG. 2 is a left side view of the device of FIG. 1 the reel placed therein.
Figure 3:
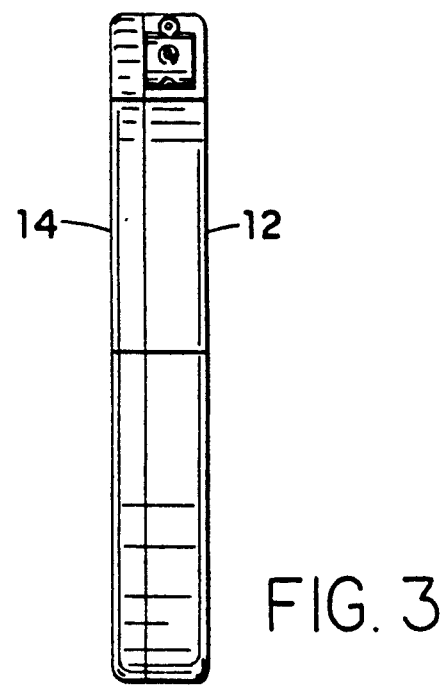
FIG. 3 is a right side view of the device of FIG. 1.

Referring to the FIGS. 1-5, there is illustrated a dispensing device 10 made in accordance with the present invention. In the particular embodiment illustrated, the dispensing device 10 comprises a base 12 and a cover 14 which are designed to snap together. In the particular embodiment illustrated, this is accomplished by providing pins 16 on base 12 which mate with aligned openings 18 in cover 14. It is to be understood that base 12 and cover 14 may be secured together by any means desired. The base 12 and cover 14 are preferably made of a clear plastic material and in the particular embodiment illustrated, are made of polycarbonate.

Rotatably mounted within dispensing device 10 is supply reel 20 and takeup reel 22. Supply reel 20 and takeup reel 22 each comprise a cylindrical center hub 26 about which a strip 25 of elastomeric material may be spirally wrapped and a side portion 29 which assists in placing the reel 20 with strip 25 in device 10 and for guiding strip 25 as it is unwound from supply reel 20. In the particular embodiment illustrated, the supply reel 20 and takeup reel 22 are rotatably mounted to base 12 by means of a pin 24 molded to base 12 which mates with its corresponding opening 27 in center hub 26. Side portion 29 has a configuration substantially that of a cylindrical disk. Take up reel 22 is positioned within the base 12 such that at least a portion of the side portion 29 extends out of the housing through opening 30. In the particular embodiment illustrated, side portion 29 extends through opening 30 such that the fingers of the user can easily contact the outer rim 31 of side portion 29. Preferably, as illustrated in the embodiment, outer rim 31 is provided with a plurality of ridges to allow easy rotation of take up reel 22 by the user.

Referring to FIG. 6, there is illustrated an enlarged view of a portion of the elastomeric strip 25 that is used within the dispensing device 10. It is, of course, understood that the elastomeric strip 25 may be provided as long as desired to accommodate the size of the reels 22, 24. The elastomeric strip 25 has a plurality of orthodontic appliances cut therein along its length. The elastomeric strip 25, in the particular embodiment illustrated, is provided with a plurality of O-rings 21 which are cut in the elastomeric strip 25 by a cutting operation. These elastomeric O-rings are maintained or connected to elastomeric strip 25 by a small connecting portion 40. In the particular embodiment illustrated, the connecting portions 40 are aligned parallel with the longitudinal axis x—x of the elastomeric strip within the dispensing device 10. Preferably, connection portion 40 is located at the trailing end with respect to the direction of movement of strip 25 in device 10 as indicated by arrow 27 as illustrated. The elastomeric strip 25 is made of a suitable material for use as an orthodontic elastomeric appliance as is presently done in the art or of any other material that elastomeric orthodontic appliances may be cut. An example of such an elastomeric strip of material of the orthodontic appliances capable of being dispensed in device 10 may be found in co-pending application Ser.

No. 119,391, filed Nov. 10, 1987 which Applicants hereby incorporate by reference herein.

Figure 7:
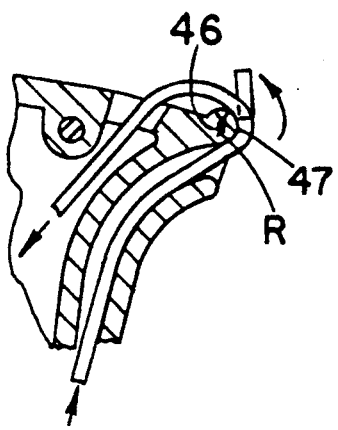
FIG. 7 is an enlarged partial view of the dispensing region of the device of FIG. 1.

Device 10 is preferably designed to be held in the palm of the hand of the user. FIG. 1 illustrates the device 10 as being held in the left hand of the user. The device 10 is provided with a dispensing region 41 which is designed to extend past the fingers of the user. Region 41 is provided with a discharge opening 42 and return opening 44 which is spaced a short distance from opening 42. Openings 42 and 44 are of sufficient size to allow the elastomeric strip 25 to easily pass therethrough. Disposed adjacent discharge opening 42 and between openings 42, 44 is a guide bar 46 which has an outer contact surface 47 about which the strip of elastomeric material is passed. Referring to FIG. 7, there is illustrated an enlarged cross sectional view of dispensing region 41. The guide bar 46 has an outer contact surface 47 which has a generally circular cross sectional shape having a radius R such that when the elastomeric strip 25 with O-rings is passed therearound, it will cause the O-ring to pop out as illustrated to allow easy removal of the O-rings with a hemostat or other appropriate tool as is presently used in the art. The radius R is preferably no greater than 0.125 inches and in the particular embodiment illustrated, the radius R is 0.05 inches.

In the preferred embodiment illustrated, reels 20, 22 are each placed in its own separate distinct compartment 33, 35 respectively. Providing of separate components minimizes or eliminates any possible cross contamination between the fresh O-rings on supply reel 20 from contacting the unused portion on the take up reel 22 thereby maintaining the aseptic qualities of the dispensed O-rings. The compartments are separated by common wall 48 formed in dispensing device 10. In the particular embodiment illustrated, wall 48 also serves to guide the strip 25 from the reel 20 to the opening 42.

In order to more fully understand the present invention, a detailed discussion of the operation thereof will now be discussed. Initially, the dispensing device is provided with a elastomeric strip 25 having a plurality of orthodontic appliances cut therein which is initially spirally wound on supply reel 20. Lead end 52 of the elastomeric strip 25 is threaded through opening 42, around guide bar 46 and back through reentry opening 44 and then is wrapped around the hub 26 of takeup reel 22. Lead end 52 of the elastomeric strip is secured to takeup reel 22 in any desired manner. In the particular embodiment, this is simply accomplished by placing the lead end 52 around hub 26 and allowing the takeup reel to be rotated several turns to allow the lead end to be wrapped about the hub 26. In order to dispense a particular orthodontic appliance, the takeup reel 22 is rotated in the appropriate direction (as illustrated by arrow 50) to cause the elastomeric strip 36 to move in the direction indicated by arrows 45 and supply reel 20 to rotate in the direction indicated by arrow 49. A small tension is experienced by strip 25 such that it wraps around guide bar 46. As an orthodontic O-ring 21 is passed around guide bar 46, this causes the free end of the O-ring 21 to pop out away from the elastomeric strip so that it may be simply pulled off with a hemostat or other appropriate device as illustrated in FIG. 5. Thereafter, the remaining portion of the elastomeric strip is taken up by takeup reel 24. It can clearly be seen that the strip 25 coming from supply reel 20 does not become exposed to the environment until rotated past the edge 46 of opening 42. This minimizes or avoids the potential contamination of any unused O-rings thus maintaining the aseptic qualities of the unused O-ring which can be used at a later time. As additional O-rings are needed, the takeup reel is rotated by rotation thereof such that successive O-rings may be taken as needed.

Figure 8:
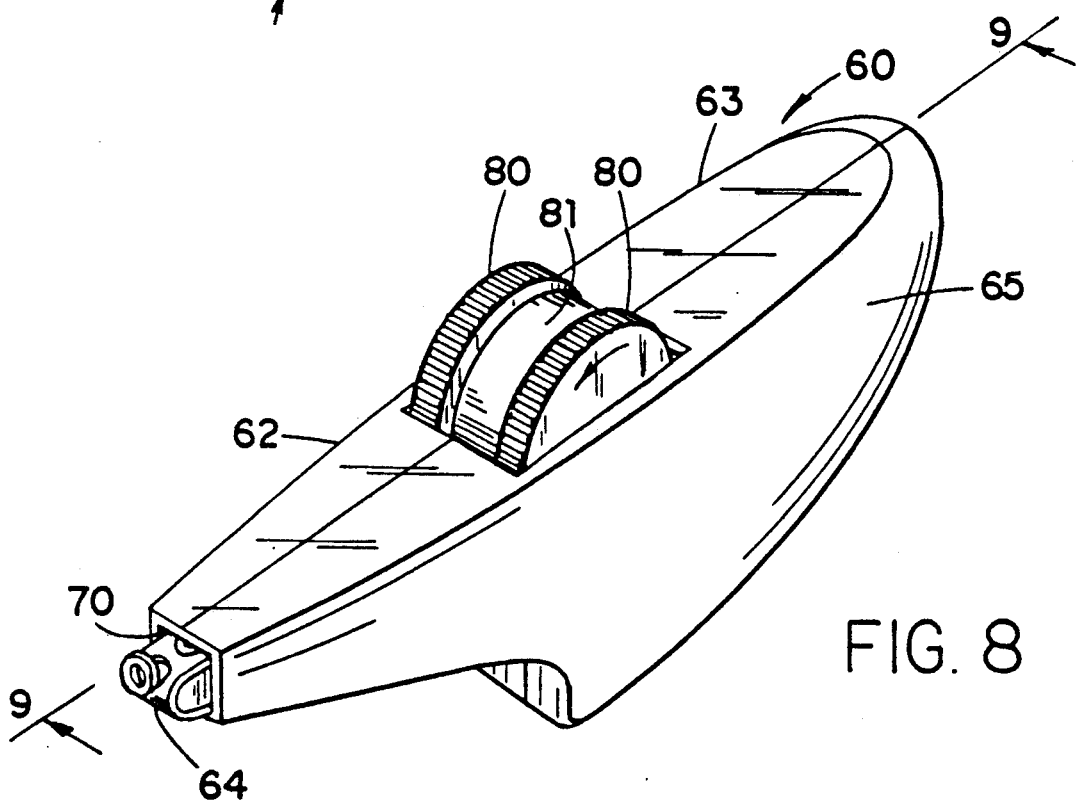
FIG. 8 is a perspective view of a modified dispensing device made in accordance with the present invention.
Figure 9:
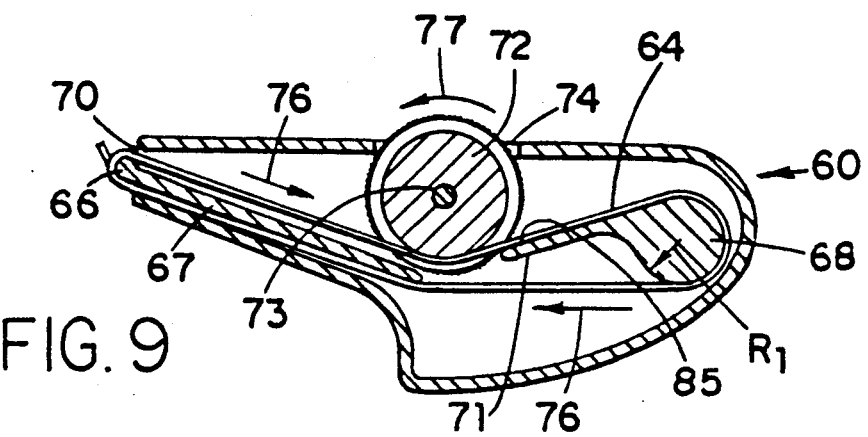
FIG. 9 is a cross sectional view of the device of FIG. 8 taken along line 9—9.

Referring to FIGS. 8-9, there is illustrated a modified dispensing device 60 made in accordance with the present invention. The device 60 includes a housing 62 comprising a left half 63 which snaps together with right half 65. It is of course understood that the right and left halves may be secured together in any manner desired. The device 60 further includes a continuous strip 64 of elastomeric material mounted therein having a plurality of orthodontic appliances cut therein. Strip 64 is identical to strip 25 illustrated in FIGS. 1-6 except that strip 64 is in the form of a closed loop. In this particular embodiment, device 60 is designed to be thrown away after a single patient use. Therefore, housing 62 is preferably made of a relatively inexpensive plastic material and the strip 64 is designed to have relatively few O-rings cut therein, for example, in the range of 10 to 20 O-rings. In the particular embodiment illustrated, strip 64 has 20 O-rings therein. The strip 64 is mounted to housing 62 by a guide bar 66 and pin 68 spaced therefrom. Extending from guide bar 66 is a wall 67 which prevents the strip from contacting itself. Guide bar 66 is positioned at the forward dispensing end of housing 62 and is adjacent dispensing opening 70. Opening 70 is of sufficient size and shape to permit O-rings to be dispensed therethrough. Guide bar 66 functions in the same manner as guide bar 46 of device 10 with regard to the presentation of the O-rings. Thus, guide bar 66 preferably has the same dimension as guide bar 46. A drive roller 72 is rotatably mounted to housing 62 by pin 73. Roller 72 is mounted such that a portion of the periphery extends out of an opening 74 in housing 62 a sufficient amount so that it can be easily rotated by a finger of the user. Roller 72 frictionally engages the outer surface of strip 64 (as shown in FIG. 9) and provides a sufficient degree of tension to strip 64 such that as roller 72 is rotated in the direction shown by arrow 77 causes strip 64 to move about guide bar 66 and pin 68 as shown by arrows 76. In the particular embodiment illustrated, the outer periphery of roller 72 is provided with a pair of axially spaced ridges 80 which forms a recess portion 81 therebetween for receiving strip 64. The ridges 80 contacts and guides the sides 85 of strip 64 which outer surface 86 of roller 72 in recess 80 contacts the flat side of strip 64 which transmits the force to move strip 64. The guide bar 66 and pin 68 are preferably made of a material having a low coefficient of friction so that strip 64 can easily slide thereon and roller 72 is preferably a structure and has a higher coefficient of friction so that it can drive strip 64 about guide bar 66 and pin 68. In the embodiment illustrated, guide bar 66 and pin 68 are made of a polypropylene or high density polyethylene and roller 72 may be made of a polycarbonate plastic. Alternatively, the roller 72 may be made of the same material as the guide bar 66 and pin 68 with the recessed portion provided with serrations (not shown) or, coated with a high co-efficient of friction material. Pin 68 has a generally circular outer surface 69 around which strip 64 is wrapped. The outer surface 69 about which strip 64 is wrapped has a radius $R_1$ of sufficient size to allow strip 64 to be easily wrapped there around. In the particular embodiment illustrated $R_1$ is about 0.25 inches. The pin 68 is further provided with a support ledge 71 which terminates prior to roller 72. Ledge 71 provides a certain degree of support to strip 64 as it moves about pin 68.

It is to be understood that the devices 10 and 60 may be packaged in its own sealed packages, for example in sealed plastic bags further assuring the aseptic nature of the orthodontic O-rings to be dispensed.

Various modifications can be made to the present invention without departing from the scope of the present invention. For example, a take up reel may not be required. The portion of the strip in which the O-rings have been removed can simply be placed into an open compartment area or removed from the dispenser. The scope of protection being defined by the following claims.

What is claimed is:

1. A dispensing device for dispensing an orthodontic elastomeric appliance formed in a strip of elastomeric material comprising:
    a housing having a discharge opening and a return opening, said return opening being spaced from said discharge opening, a guide bar adjacent said discharge opening and being disposed between said discharge opening and return opening;
    a supply reel rotatably mounted in said housing for holding a strip of elastomeric material having a plurality of orthodontic appliances formed therein, each of said orthodontic appliances being connected to said strip of elastomeric material by a breakable connecting portion;
    a takeup reel rotatably mounted in said housing, said takeup reel capable of receiving the unused portion of the elastomeric strip from which said orthodontic appliance are removed, said elastomeric strip being mounted in said housing such that it passes from said supply reel out said discharge opening around said guide bar back into said housing through said re-entry opening and on to the takeup reel;
    drive means for rotating said takeup reel causing the elastomeric strip to unwind from said supply reel and exit out said discharge opening around said guide bar for dispensing of said elastomeric appliance.

2. A dispensing device according to claim 1 wherein said housing further comprises a first compartment and second compartment, said supply reel is placed in said first compartment and said takeup reel is placed in said second compartment.

3. A dispensing device according to claim 2 wherein said drive means for causing said strip to unwind comprises rotating said takeup reel.

4. A dispensing device according to claim 1 wherein said guide bar has an outer radius no greater than about 0.125 inches.

5. A dispensing device according to claim 1 wherein said guide has an outer radius of about 0.05 inches.

6. A dispensing device for dispensing orthodontic elastomeric appliances formed in a strip of elastomeric material comprising:
    a housing having a discharge opening and a guide bar adjacent said discharge opening;
    a strip of elastomeric material having a plurality of orthodontic appliances formed therein, each of said orthodontic appliances being connected to said strip of elastomeric material by a breakable connecting portion;
    said strip being mounted in said housing such that it passes out said discharge opening around said guide bar;
    means for moving said elastomeric strip out said discharge opening around said guide bar for dispensing of said elastomeric appliances.

7. A dispensing device according to claim 6 wherein said guide bar has an outer radius no greater than about 0.125 inches.

8. A dispensing device according to claim 6 wherein said guide has an outer radius of about 0.05 inches.

9. A dispensing device for dispensing orthodontic elastomeric appliances formed in a strip of elastomeric material comprising:
    a housing having a discharge opening and a pair of spaced pins therein, one of said pins positioned adjacent said discharge opening;
    an elastomeric strip in the form of a continuous loop mounted in said housing around said pair of pins, each of said orthodontic appliances being connected to said strip of elastomeric material by a breakable connecting portion;
    drive means for rotating elastomeric strip so as to dispense said elastomeric appliance out said discharge opening.

10. A dispensing device according to claim 9 wherein said guide bar has an outer radius no greater than about 0.125 inches.

11. A dispensing device according to claim 9 wherein said guide has an outer radius of about 0.05 inches.

* * * * *